(12) United States Patent
Dimitrova et al.

(10) Patent No.: US 9,528,113 B2
(45) Date of Patent: Dec. 27, 2016

(54) THERAPY DELIVERY AND MONITORING USING A GENE OF INTEREST-REPORTER FUSION PROTEIN AND OPTICAL IMAGING

(75) Inventors: Nevenka Dimitrova, Briarcliff Manor, NY (US); Chetan Mittal, Bangalore (IN)

(73) Assignee: Koninklijke Philips N.V., Eindhoven (NL)

( * ) Notice: Subject to any disclaimer, the term of this patent is extended or adjusted under 35 U.S.C. 154(b) by 576 days.

(21) Appl. No.: 12/993,109

(22) PCT Filed: May 14, 2009

(86) PCT No.: PCT/IB2009/052010
§ 371 (c)(1),
(2), (4) Date: Nov. 17, 2010

(87) PCT Pub. No.: WO2009/147549
PCT Pub. Date: Dec. 10, 2009

(65) Prior Publication Data
US 2011/0189098 A1 Aug. 4, 2011

(30) Foreign Application Priority Data
May 27, 2008 (EP) .................... 08104122

(51) Int. Cl.
*G01N 33/00* (2006.01)
*C12N 15/62* (2006.01)
*C07K 14/435* (2006.01)
*C07K 14/71* (2006.01)
*C12Q 1/68* (2006.01)

(52) U.S. Cl.
CPC ......... *C12N 15/62* (2013.01); *C07K 14/43595* (2013.01); *C07K 14/71* (2013.01); *C12Q 1/6897* (2013.01); *C07K 2319/60* (2013.01)

(58) Field of Classification Search
None
See application file for complete search history.

(56) References Cited

U.S. PATENT DOCUMENTS

| 6,649,159 B2 * | 11/2003 | Yang et al. .......... 424/93.21 |
| 2002/0107362 A1 | 8/2002 | Thastrup |
| 2004/0181821 A1 | 9/2004 | Zhou |
| 2007/0274908 A1 | 11/2007 | Pasqualini |

FOREIGN PATENT DOCUMENTS

| JP | 2007186492 | * | 6/2007 |
| WO | 9954348 A1 | | 10/1999 |
| WO | 0129235 A2 | | 4/2001 |
| WO | 0224930 A2 | | 3/2002 |
| WO | 2004043992 A1 | | 5/2004 |
| WO | WO2004/111190 | * | 12/2004 |
| WO | 2006099019 A2 | | 9/2006 |
| WO | 2007046803 A1 | | 4/2007 |
| WO | 2007109335 A2 | | 9/2007 |
| WO | 2007128982 A2 | | 11/2007 |
| WO | 2007140319 A1 | | 12/2007 |
| WO | 2008138572 A1 | | 11/2008 |

OTHER PUBLICATIONS

Hakkarainen et al (International Journal of Molecular Medicine, 2006. vol. 18, pp. 751-759).*
Schrump et al (Seminar in Oncology, 2005. vol. 32, pp. 488-502).*
Semizarov et al. (Proceedings of National Academy of Sciences 2003. vol. 100, No. 11, pp. 6347-6352).*
Tsunoda et al (Biochemical and Biophysical Research Communication, 2005. vol. 336, pp. 118-127).*
Schiffelers et al (Nucleic Acid Research, 2004. vol. 32, No. 19, pp. 1-10).*
Lembo, F. et al. "MBDin, a Novel MBD2-Interacting Protein, Relieves MBD2 Repression Potential and Reactivates Transcription from Methylated Promoters". Molecular and Cellular Biology, Mar. 2003, p. 1656-1665.
Chan, Y. et al. "The Cell-specific Expression of Endothelial Nitric-oxide Synthase". The Journal of Biological Chemistry. vol. 279, No. 3, Issue of Aug. 13, 2004, pp. 35087-35100.
Bhattacharya, R. et al. "Efficacy of vaccination with plasmid DNA encoding for HER2/neu or HER2/neu-EGFP fusion protein against prostate cancer in rats". International Immunopharnacology 2 (2002) 783-796.
Medarova, Zdravka et al "In Vivo Imaging of SiRNA Delivery and Silencing in Tumors", Technical Reports, Nature Medicine, vol. 13, No. 3, Mar. 2007.
Lewis, David L. "Efficient Delivery of SiRNA for Inhibition of Gene Expression in Postnatal Mice" Nature Genetics, vol. 32,Sep. 2002.
McCaffrey, Anton P. et al "Gene Expression : RNA Interference in Adult Mice", Nature, No. 418, Jul. 2002.
Takeshita, Fumitaka et al "Efficient Delivery of Small Interfering RNA to Bone-Metastatic Tumors by using Atelocollagen in Vivo", PNAS, vol. 102, No. 34, Aug. 2005.

(Continued)

Primary Examiner — Celine Qian

(57) ABSTRACT

The present invention relates to a method of non-invasively monitoring the expression of a gene of interest in a cell when contacting said cell with a compound influencing the expression of said gene of interest. The present invention is also concerned with different isolated nucleic acid molecules comprising a coding sequence. Said coding sequence comprises a gene of interest-sequence encoding a gene of interest-polypeptide fused to a reporter sequence encoding a fluorescent reporter polypeptide and is operatively coupled to a promoter sequence. The present invention is also concerned with the use of a method and a nucleic acid molecule of the invention for delivering a compound influencing the expression of a gene of interest in a cell, monitoring the delivery of said compound as well as monitoring the influence on the expression of said gene of interest induced by said compound at the same time.

11 Claims, 1 Drawing Sheet

(56) References Cited

OTHER PUBLICATIONS

Detich, Nancy et al "Promoter-Specific Activation and Demethylation by MBD2/Demethylase", The Journal of Biological Chemistry, vol. 277, No. 39, Sep. 2002, pp. 35791-35794.

Fukumura, Dai et al "Tumor Induction of VEGF Promoter Activity in Stromal Cells", Cell, vol. 94, Sep. 1998, pp. 715-725.

Chalfie, Martin et al "Green Fluorescent Protein as a Marker for Gene Expression", Science, vol. 263, Feb. 1994, pp. 802-805.

* cited by examiner

Step 1, 2: Transfection of Gene-FP construct
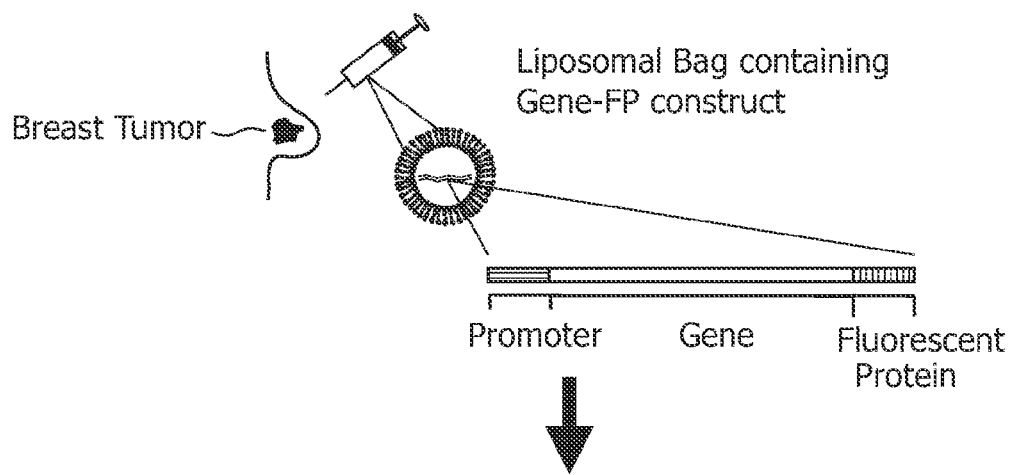
Step 3: Visualization of gene translation using optical imaging
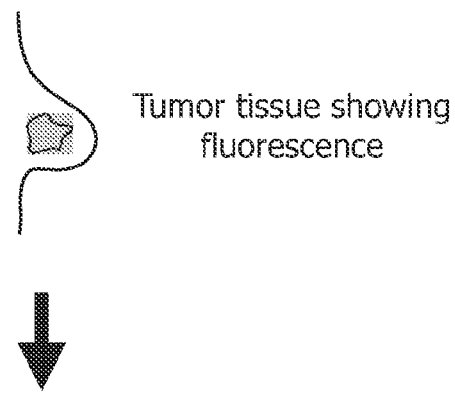
Step 4: Transfection of RNAi
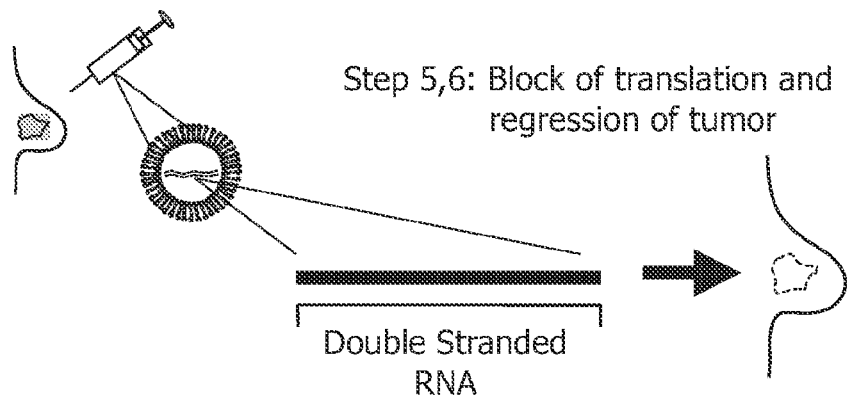

THERAPY DELIVERY AND MONITORING USING A GENE OF INTEREST-REPORTER FUSION PROTEIN AND OPTICAL IMAGING

FIELD OF THE INVENTION

The present invention relates to a method of non-invasively monitoring the expression of a gene of interest in a cell when contacting said cell with a compound influencing the expression of said gene of interest.

Thus, the invention is concerned with a method of monitoring the increase in the expression of a gene of interest in a cell when contacting said cell with a demethylating drug. The invention is also concerned with monitoring the decrease in the expression of a gene of interest in a cell when contacting said cell with an RNAi. Said methods may be performed in vivo or outside the human or animal body.

The present invention is also concerned with different nucleic acid molecules comprising sequences encoding a gene of interest-polypeptide and a fluorescent reporter polypeptide.

BACKGROUND OF THE INVENTION

One of the major tasks of today's medicine is the development of a therapeutic system which is capable of selectively influencing the expression of a gene suspicious of being misregulated or known to be misregulated. Depending on the gene(s) affected, this may manifest in severe diseases such as e.g. cancer. Although there has been a lot of effort in this field, there is still the need to improve the results gained thus far and combine them e.g. with a system capable of easily monitoring the therapeutic effect and/or the delivery of the therapeutic compound.

In general, the concept of gene expression can be summarized as to include several steps: on the DNA-level, a specific sequence is coding for a protein or an RNA, both of which may exhibit a specific function. In a first step, the DNA is transcribed into corresponding RNA. This step is tightly controlled including so called promoter regions, often at the 5'-end and in close proximity to the coding sequence, as well as further up- or downstream regulatory DNA elements and transcription factors positively and negatively influencing transcription. In case a protein is the final product of the expression of a gene, the transcribed RNA is referred to as mRNA. In a second step, this mRNA is translated into protein and said protein is then in a subsequent step optionally further modified post-translationally. In case an RNA is the final product, the transcribed RNA may be rearranged and processed as well as included in complexes comprising e.g. proteins. Thus, it is possible to influence gene expression on a DNA-level by e.g. targeting factors influencing the first step, namely transcription. Also, the second step may be targeted: in case of a protein as final product, translation of the mRNA, in case of an RNA as final product, the processing etc. may be blocked. If a method ultimately results in the degradation of the transcribed RNA, no final product can be obtained and thus the second step is inhibited.

In case a disease is caused by downregulation of a gene or even by its complete silencing, the therapeutic effect should be the upregulation of said endogenous gene to a normal level. For certain types of cancer, for example, prominent tumour-suppressor genes are known to be silenced and thus unable to exhibit their corresponding tumour-suppressor function. DNA-methylation has been identified as a major reason for gene-downregulation/silencing. Said methylation is often found in the promoter regions of the corresponding genes. In these cases, gene expression may be restored by removing methyl groups from the DNA. Downregulation/silencing of a gene may also be due to the upregulation of a transcription factor which is acting as negative transcription factor for this gene, thus blocking the expression of the gene. In these cases, therapy should be directed to a downregulation of the gene encoding the transcription factor and thus lowering the level of the transcription factor.

If upregulation of a gene is causative for a disease, the therapeutic effect should correspondingly be the downregulation of said endogenous gene to a normal level. In almost all types of cancers, genes are known to be upregulated. They are commonly referred to as oncogenes or proto-oncogenes wherein proto-oncogenes may not directly have an effect on e.g. the proliferation of a cell but indirectly by e.g. causing other genes to be upregulated. RNAi-methods may be used in order to downregulate gene-expression. In contrast to demethylating drugs which are directly acting on the "DNA-level", RNAi-methods typically act on the second step of gene expression, namely on the translation into protein or the processing into corresponding RNA. These methods ultimately lead to the degradation of the transcribed RNA. Thus, the entire process of gene expression is blocked by RNAi. This may also be referred to as "silencing" of a gene by RNAi. Mechanistically, the artificially introduced "RNA" (e.g. transcribed from a vector, introduced as RNA-duplex, etc.) is processed, and one strand is incorporated into a complex which recognizes transcribed RNA in a sequence specific manner. Thus, the sequence of the introduced RNA specifies the targeted "gene to be silenced". Following hybridization, recognition and complex formation, the targeted RNA is degraded by further mechanisms.

Current methods of monitoring the effect of therapeutic systems influencing the expression of genes mainly rely on comparing the status of a disease, e.g. a tumour, before and after the therapeutic system is applied. Thus, e.g. X-ray- or ultrasound-methods may be used to determine the size of a tumour prior to and following the treatment. However, with such systems it is neither possible to directly monitor the effect of said treatment on the gene expression nor to analyze whether the corresponding compound localized to the affected tissue at all. Other methods require tissue-samples in order to determine the result of a treatment. Thus, a biopsy or even surgical steps are necessary, which are often accompanied by additional problems such as infections. Furthermore, again only an ex post analysis is possible.

As a consequence, there is a need to establish or improve therapies influencing gene expression and methods that allow monitoring the application and the effect of these therapies on the expression of targeted genes in a non-invasive manner.

OBJECTS AND SUMMARY OF THE INVENTION

It is an objective of the present invention to provide methods and compounds for non-invasively monitoring the expression of a gene of interest in a cell when contacting said cell with a compound influencing the expression of said gene of interest.

These and other objectives of the present invention, as they will become apparent from the ensuing description, are solved by the subject matter of the independent claims. The dependent claims relate to some of the preferred embodiments of the invention.

According to one aspect of the invention, a method of non-invasively monitoring the expression of a gene of interest in a cell is provided, comprising at least the steps of:
  a) Introducing a nucleic acid molecule comprising:
    aa) a promoter sequence;
    bb) operatively linked thereto a sequence encoding said gene of interest polypeptide;
    cc) operatively fused thereto a sequence encoding a fluorescent reporter polypeptide;
  into said cell;
  b) Detecting the fluorescent reporter polypeptide in said cell by a non-invasive optical imaging method;
  c) Contacting said cell with a compound influencing the expression of said gene of interest;
  d) Detecting the fluorescent reporter polypeptide in said cell by a non-invasive optical imaging method upon step c);
  e) Comparing the level of fluorescent reporter polypeptide detected in step b) to the level of fluorescent reporter polypeptide detected in step d);
  f) Assigning the change in the expression of said gene of interest induced by said compound based on the comparison in step e).

In a preferred embodiment related to the method as described above, the present invention describes a method of non-invasively monitoring in vivo the expression of a gene of interest in a cell comprising at least the steps of:
  a) Introducing a nucleic acid molecule comprising:
    aa) a methylated promoter sequence;
    bb) operatively linked thereto a sequence encoding said gene of interest polypeptide;
    cc) operatively fused thereto a sequence encoding a fluorescent reporter polypeptide;
  into said cell;
  b) Detecting the fluorescent reporter polypeptide in said cell by a non-invasive optical imaging method;
  c) Contacting said cell with a demethylating drug;
  d) Detecting the fluorescent reporter polypeptide in said cell by a non-invasive optical imaging method upon step c);
  e) Comparing the level of fluorescent reporter polypeptide detected in step b) to the level of fluorescent reporter polypeptide detected in step d);
  f) Assigning the increase in the expression of said gene of interest induced by the demethylating drug based on the comparison in step e).

The present invention describes in a further preferred embodiment a method of non-invasively monitoring the expression of a gene of interest comprising at least the steps of:
  a) Introducing a nucleic acid molecule comprising:
    aa) a methylated promoter sequence;
    bb) operatively linked thereto a sequence encoding said gene of interest polypeptide;
    cc) operatively fused thereto a sequence encoding a fluorescent reporter polypeptide; into a cell which is outside the human or animal body;
  b) Detecting the fluorescent reporter polypeptide in said cell by a non-invasive optical imaging method;
  c) Contacting said cell with a demethylating drug;
  d) Detecting the fluorescent reporter polypeptide in said cell by a non-invasive optical imaging method upon step c);
  e) Comparing the level of fluorescent reporter polypeptide detected in step b) to the level of fluorescent reporter polypeptide detected in step d);
  f) Assigning the increase in the expression of said gene of interest induced by the demethylating drug based on the comparison in step e).

Another embodiment of the present invention relates to an isolated nucleic acid molecule that can be used for the afore-mentioned methods comprising
  a) a methylated promoter sequence;
  b) operatively linked thereto a sequence encoding a gene of interest polypeptide;
  c) operatively fused thereto a sequence encoding a fluorescent reporter polypeptide.

The coding sequence comprising the sequence encoding a gene of interest polypeptide fused to the sequence encoding a fluorescent reporter polypeptide comprises a single start-codon at the 5'-end and single stop-codon at the 3'-end. The term "single start codon" as used herein does not exclude the presence of other internal ATG codons. These latter codons, however, should not initiate translation.

In a preferred embodiment of the present invention, the gene of interest is in this aspect of the invention is a tumour-suppressor gene or a gene suspicious of being causative for a disease due to its silencing.

Thus, in a further preferred embodiment, the present invention relates to an isolated nucleic acid molecule that can be used for the afore-mentioned methods comprising
  a) a methylated promoter sequence;
  b) operatively linked thereto a sequence encoding a polypeptide selected from the group of polypeptides comprising CADM1, Rb, ZMYND10, RASSF5, PTEN, SERPINB5, EPB41L3 and DAPK1;
  c) operatively fused thereto a sequence encoding a fluorescent reporter polypeptide;
    wherein the coding sequence comprised of b) and c) comprises a single start-codon at the 5'-end and a single stop-codon at the 3'-end.

Preferably, the sequence referred to in item b) above is selected from CADM1.

In another preferred embodiment, the present invention describes a method of non-invasively monitoring the decrease in the expression of a gene of interest in a cell in vivo comprising at least the steps of:
  a) Introducing a nucleic acid molecule comprising:
    aa) a promoter sequence;
    bb) operatively linked thereto a sequence encoding a non-functional polypeptide of said gene of interest;
    cc) operatively fused thereto a sequence encoding a fluorescent reporter polypeptide;
  into said cell;
  b) Detecting the fluorescent reporter polypeptide in said cell by a non-invasive optical imaging method;
  c) Contacting said cell with RNAi tailored against said gene of interest;
  d) Detecting the fluorescent reporter polypeptide in said cell by a non-invasive optical imaging method upon step c);
  e) Comparing the level of fluorescent reporter polypeptide detected in step b) to the level of fluorescent reporter polypeptide detected in step d);
  f) Assigning the decrease in the expression of said gene of interest induced by the RNAi based on the comparison in step e).

The present invention further relates to a nucleic acid molecule which can be used in such a method comprising:
  a) a promoter sequence;
  b) operatively linked thereto a sequence encoding a non-functional polypeptide of a gene of interest;

c) operatively fused thereto a sequence encoding a fluorescent reporter polypeptide;

The coding sequence comprising the sequence encoding a non-functional polypeptide of a gene of interest fused to the sequence encoding a fluorescent reporter polypeptide comprises a single start-codon at the 5'-end and single stop-codon at the 3'-end. The term "single start codon" as used herein does not exclude the presence of other internal ATG codons. These latter codons, however, should not initiate translation.

In a preferred embodiment of this aspect of the invention, the gene of interest-sequence encoding the non-functional gene of interest polypeptide comprises either a part of the entire gene of interest-sequence or the entire gene of interest-sequence containing at least one insertion, at least one deletion, at least one nucleotide exchange, or mixtures thereof. Thereby a non-functional gene of interest polypeptide is obtained. However, the gene of interest-region does not comprise stop-codons.

Furthermore, in an even more preferred embodiment of this aspect, the present invention describes a nucleic acid molecule as outlined in the previous two paragraphs above, wherein the gene of interest is an oncogene, a proto-oncogene or a gene suspicious of being causative for a disease due to its overexpression.

Thus, in a further preferred embodiment, the present invention relates to an isolated nucleic acid molecule that can be used for the afore-mentioned methods comprising
 a) a promoter sequence;
 b) operatively linked thereto a sequence encoding a non-functional polypeptide selected from the group of polypeptides comprising VEGF, RAS, Wnt, MYC, ERK and TRK;
 c) operatively fused thereto a sequence encoding a fluorescent reporter polypeptide;
  wherein the coding sequence comprised of b) and c) comprises a single start-codon at the 5'-end and a single stop-codon at the 3'-end.

Preferably, the sequence referred to in item b) above is selected from VEGF and/or Wnt.

Thus, in a corresponding preferred embodiment of this aspect of the invention, the sequence encoding the non-functional polypeptide selected from the group of polypeptides comprising VEGF, RAS, Wnt, MYC, ERK and TRK comprises either a part of the entire sequence or the entire sequence containing at least one insertion, at least one deletion, at least one nucleotide exchange, or mixtures thereof, in order to obtain a non-functional polypeptide. However, the sequence does not comprise stop-codons.

In a further embodiment relating to this aspect, the present invention relates to an isolated nucleic acid molecule comprising
 a) a promoter sequence;
 b) operatively linked thereto a sequence encoding a non-functional polypeptide of Her-2neu wherein said sequence contains at least one insertion, at least one nucleotide exchange, or mixtures thereof, in order to obtain a non-functional polypeptide, but wherein the sequence does not comprise stop-codons;
 c) operatively fused thereto a sequence encoding a fluorescent reporter polypeptide;
  wherein the coding sequence comprised of b) and c) comprises a single start-codon at the 5'-end and a single stop-codon at the 3'-end.

In an even further aspect of the present invention, a method is disclosed wherein a decrease in the expression of a gene of interest is non-invasively monitored in a cell outside the human or animal body comprising at least the steps of:
 a) Introducing a nucleic acid molecule comprising:
  aa) a promoter sequence;
  bb) operatively linked thereto a sequence encoding said gene of interest polypeptide;
  cc) operatively fused thereto a sequence encoding a fluorescent reporter polypeptide;
  into a cell which is outside the human or animal body;
 b) Detecting the fluorescent reporter polypeptide in said cell by a non-invasive optical imaging method;
 c) Contacting said cell with RNAi tailored against said gene of interest;
 d) Detecting the fluorescent reporter polypeptide in said cell by a non-invasive optical imaging method upon step c);
 e) Comparing the level of fluorescent reporter polypeptide detected in step b) to the level of fluorescent reporter polypeptide detected in step d);
 f) Assigning the decrease in the expression of said gene of interest induced by the RNAi based on the comparison in step e).

In the embodiments of the in vivo and in vitro methods as outlined above, said nucleic acid molecule and/or said RNAi may be introduced into said cell by transfection with the help of sonoporation, local injection or liposomal bags carrying antibodies to the host cell antigens for correct targeting, identification and localisation, or mixtures thereof.

Yet another aspect of the invention relates to the use of methods as disclosed above.

Said methods may be applied in vivo or outside the human or animal body. In one embodiment, said method is used for monitoring the expression of a gene of interest in a cell over time when contacting said cell with a compound influencing the expression of said gene of interest and thus for monitoring the effect of said compound.

In a further embodiment, the method as disclosed above may be used for delivering a compound influencing the expression of a gene of interest in a cell, monitoring the delivery of said compound as well as monitoring the influence on the expression of said gene of interest induced by said compound at the same time. Again, this applies for the in vivo situation as well as for the method performed in a cell outside the human or animal body.

In another preferred embodiment, a method as described above, either in vivo or outside the human or animal body, is used for adjusting the dosage of a compound influencing the expression of a gene of interest in order to obtain a further change in the expression of said gene of interest.

In another aspect of the invention, a method related to the use of a demethylating drug is used for testing different demethylating drugs in one embodiment in order to identify the most potent demethylating drug separately or in combination.

This aspect relates in a further preferred embodiment to the methods comprising RNAi. Thus, said method is used for testing different RNAi's tailored against one gene of interest in order to identify the most potent RNAi separately or in combination.

DESCRIPTION OF THE FIGURES

FIG. 1 depicts schematically and exemplary steps of a possible application of the present invention, namely of RNAi therapy and its monitoring in breast cancer tissue.

The steps are described in detail in the example section of the present application.

DETAILED DESCRIPTION OF THE INVENTION

The inventors have found that it is possible to non-invasively monitor the expression of a gene of interest in a cell. This system may be used when a compound influencing the expression of said gene of interest is contacted with a cell.

While describing in detail exemplary embodiments of the present invention, definitions important for understanding the present invention are provided.

As used in the specification and the appended claims, the singular form of "a" and "an" also includes the respective plurals unless the context clearly dictates otherwise.

In the context of the present invention, the term "about" and "approximately" denote an interval of accuracy that a person skilled in the art will understand to still ensure the technical effect of the feature in question. The term typically indicates a deviation from the indicated numerical value of ±10% and preferably ±5%.

It is to be understood that the term "comprising" is not limiting. For the purpose of the present invention, the term "consisting of" is considered to be a preferred embodiment of the term "comprising of". If hereinafter a group is defined to comprise at least a certain number of embodiments, this is also meant to encompass a group that preferably consists of these embodiments only.

As has been set out above, the present invention refers to a method of non-invasively monitoring the expression of a gene of interest in a cell when contacting said cell with a compound influencing the expression of said gene of interest. Thus, the invention relates in one embodiment to a method of non-invasively monitoring the expression of a gene of interest in a cell comprising at least the steps of:
  a) Introducing a nucleic acid molecule comprising:
    aa) a promoter sequence;
    bb) operatively linked thereto a sequence encoding said gene of interest polypeptide;
    cc) operatively fused thereto a sequence encoding a fluorescent reporter polypeptide;
  into said cell;
  b) Detecting the fluorescent reporter polypeptide in said cell by a non-invasive optical imaging method;
  c) Contacting said cell with a compound influencing the expression of said gene of interest;
  d) Detecting the fluorescent reporter polypeptide in said cell by a non-invasive optical imaging method upon step c);
  e) Comparing the level of fluorescent reporter polypeptide detected in step b) to the level of fluorescent reporter polypeptide detected in step d);
  f) Assigning the change in the expression of said gene of interest induced by said compound based on the comparison in step e).

In the context of the present invention, the term "non-invasively" monitoring means that during the detection steps b) and d) of the method of the invention, no direct physical contact with the cell and/or the monitored tissue of a patient is needed in order to monitor the expression of a gene of interest. Thus, neither a surgery, nor a biopsy nor any other method involving contact with the cell (such as patch-clamping in in vitro assays) during the detection steps are needed.

"Monitoring" refers in its general meaning to a process of determining a parameter and keeping track of the parameter over time.

The term "expression of a gene of interest" as used herein comprises at least two steps. Thus, transcription of the gene of interest into corresponding RNA is one step of gene expression. In case a protein is encoded by the gene, said RNA is referred to as mRNA. The RNA can be further processed (e.g. spliced) and, in a second step, the mRNA is translated into protein. Proteins may thus be the final products of gene expression. The amount of a protein as final product may correlate with the level of gene expression. However, also RNA-molecules may be the final products of gene expression. Said RNAs may also be subject of processing and modification in a second step.

The term "a compound influencing the expression of a gene" as used herein comprises any compound having a positive or negative impact on the endogenous gene expression.

Such a compound may act on the DNA-level. This means that said compound may influence e.g. the methylation state of the DNA or lead to structural rearrangements of DNA, e.g. from a closed to an open conformation, without influencing the DNA-sequence. As DNA-methylation (especially in a promoter region) is known to cause silencing of the corresponding gene, compounds acting as demethylating drugs are known to increase gene expression due to the removal of methyl groups from DNA. Histone-deacetylases (HDACs) remove acetyl-groups from DNA and are implicated in gene repression. Thus, compounds inhibiting HDACs may have a positive influence on gene expression as well. These drugs, commonly referred to as HDAC-inhibitors, will also be mentioned below. However, in one embodiment of the present invention, compounds positively influencing gene expression are encompassed.

In a further preferred embodiment of the present invention, compounds may be used that act on the second step of gene expression, namely on the transcribed RNA. In case said RNA is degraded, gene-expression is negatively influenced. In this embodiment of the invention, e.g. RNAi's may be employed in order to inhibit the translation step. Such RNAi's include siRNA, shRNA, miRNA etc. as set out in detail below.

"Contacting a cell" as used herein comprises any way known to the person skilled in the art to deliver a compound such that it can exert its effect on the cell. This may be done in vivo e.g. by i.v. injection, topical application, inhalation, etc. For cell culture systems, a compound such as a demethylating drug may simply be added to the cell culture medium used for cultivation. However, also transfection methods as outlined below may be used in order to bring a compound in contact with a cell and, in a next step, said compound may be introduced into said cell.

The term "nucleic acid molecule" refers in the context of the present invention to DNA, RNA, or derivatives thereof. Preferably, it refers to double stranded DNA molecules. Said nucleic acid molecules may be circular or linear, dependent on the mechanism which is used to introduce said nucleic acid molecules into a cell.

The term "introducing into a cell" in the context of the present invention defines that a nucleic acid molecule, e.g. DNA or RNA, is introduced in the corresponding cell by any method known to the person skilled in the art. "Introducing" furthermore implies that said nucleic acid molecule is present in the cell such that coding sequences present on said nucleic acid molecule may be expressed dependent on how such regions are regulated. To this end, techniques such as transfection methods as depicted in detail below may be used.

In the context of the present invention, the term "coding region" or "coding sequence" is meant to encompass a DNA-sequence which starts at the 5'-end with the Start-codon, i.e. ATG. This triplet codes for the first amino acid, a methionine, of the corresponding protein when translation of the mRNA is initiated. Accordingly, the coding region ends at the 3'-end with a Stop-codon, e.g. TAG, in order to terminate protein translation. It is important to note that for the present invention no stop-codons are present anywhere within the coding sequence except for the one mentioned above at the 3' end. Thus, in summary, the entire coding sequence is transcribed into one corresponding mRNA. Translation of the mRNA results in one protein which may be comprised of at least two different domains/polypeptides/parts. However, as pointed out in detail below, said polypeptides do not necessarily need to be functional; however, for all coding sequences at least two sequences coding for at least two polypeptides may be present within said one coding sequence.

In a preferred embodiment of the present invention, said coding sequence of the nucleic acid molecule comprises a single start codon at the 5'-end and a single stop-codon at the 3'-end. The term single start codon as used herein means that the sequence may comprise further internal ATG codons which, however, may not be used to initiate translation.

The terms "gene of interest sequence", "gene of interest region" and "sequence encoding said gene of interest polypeptide" refer to a DNA sequence of the gene of interest to be monitored by the method of the present invention. In the context of the present invention, preferably genes are encompassed by said term, which translate into proteins and which are suspicious of being causative for certain diseases due to misregulation. This will be outlined in detail below. Thus, such sequences preferably comprises only the coding region of a gene, i.e. only exons and no introns. However, in certain embodiments it may be applicable to also use intron regions of a gene of interest.

In the following, the terms "reporter polypeptide" as well as "reporter" will be explained in detail. This paragraph refers to all embodiments of the present invention, i.e. to all methods mentioned in detail below as well as to all nucleic acid molecules that are encompassed by the present invention. It is important to note that the sequence encoding a reporter polypeptide is always in frame with the sole ATG at the 5'-end of the coding sequence such that the corresponding polypeptide is always correctly expressed, i.e. a functional polypeptide/protein is made. Furthermore, in all embodiments of the present invention, the nucleic acid sequences encoding reporter polypeptides encode fluorescent reporter polypeptides. Said fluorescent reporter polypeptide may be selected from a blue, green, cyan, red or infrared fluorescent protein. In an especially preferred embodiment of the present invention, the reporter sequence encodes a green fluorescent protein.

The term "operatively fused" as used in the present invention defines that at least two DNA regions (e.g. the sequence encoding the gene of interest polypeptide as well as the sequence encoding the reporter polypeptide) are linked to each other. Thus, they may in one preferred embodiment form one coding sequence for one expression product, i.e. one protein, which is comprised of at least two different domains/polypeptides. Thus, as mentioned above, there is only one open reading frame coding for the corresponding protein, wherein the sequence encoding the reporter polypeptide is always in frame with said open reading frame in order to have a functional reporter polypeptide expressed. Preferably, the gene of interest sequence is fused 5' to the reporter sequence in order to encode a protein, which is made of a gene of interest polypeptide followed by a fluorescent reporter polypeptide.

In a further preferred embodiment of the present invention, the coding regions of such nucleic acid molecules may additionally comprise a spacing region encoding a polypeptide spacer in-between the fused gene of interest- and reporter sequences. Also in this case, the spacer region is always in frame with said open reading frame in order to have a functional spacing polypeptide expressed.

The term "operatively linked" means that the expression of the coding region as defined above is mechanistically controlled by other regions, such as promoters or enhancers. These regions are usually other DNA region also present in the nucleic acid molecule. Such operatively linked regions may be anywhere on the nucleic acid molecule; however, they are preferably present as regulatory regions such as promoters 5' to the coding sequence.

In the context of controlling the expression of a coding sequence, the term "promoter sequence" or simply "promoter" refers to a defined DNA sequence, which is influencing the expression of genes. Thus, a typical promoter sequence is comprised of a defined base-sequence of a certain length being recognised by certain cellular factors. Often, these factors bind to these conserved sequences and act as positive or negative regulators of gene expression and are therefore commonly referred to as "transcription factors". Many promoter sequences are known to the person skilled in the art and even a combination of different promoter sequences in artificial nucleic acid molecules is possible.

Depending on the method of the present invention, different promoters may be used. The nucleic acid molecule according to the invention may thus comprise in a preferred embodiment a promoter sequence wherein said promoter sequence is a human promoter identified by at least one human transcription factor inducing the expression of said coding sequence. Furthermore, said human promoter may be a strong, constitutively active promoter. In other embodiments, said human promoter may be a strong inducible, e.g. tissue-selective, promoter. In certain embodiments, it may also be a viral promoter. In a most preferred embodiment of the invention, the promoter sequence of the nucleic acid molecule regulating the expression of the coding sequence comprising inter alia the gene of interest sequence may be the endogenous promoter sequence (i.e. the sequence regulating the expression of the endogenous gene of interest), thus reflecting the endogenous situation.

The term "detecting by a non-invasive optical imaging method" refers to any method which may be used in order to non-invasively detect the fluorescent reporter polypeptides in a cell. As the method is dependent on the reporter polypeptide, it allows to gain insights into the functional and biochemical properties of said polypeptide as well as of the cell, the polypeptide is expressed in. "Optical imaging" methods typically rely on such agents, generally referred to as contrast agents; in the present invention, the fluorescent reporter polypeptides represent said contrast agents.

Preferably, the detection of the fluorescent reporter polypeptides according to the method of the present invention is done by fluorescence microscopy, fluorescence imaging, single photon and multi-photon confocal microscopy, laser induced fluorescence etc. As a fluorescent protein emits a colour of a certain wavelength upon excitation, the fluorescent protein in a cell needs to be excited by employing light of a certain excitation wavelength followed by the detection of light of the emitted wavelength (GFP for example is excited by UV-light and emits light of a wavelength corresponding to a green colour). Thus, the imaging methods used in the present invention refer to devices which emit light at a certain wavelength in order to excite the fluorescent polypeptides and detect light at a certain wavelength emitted by the fluorescing polypeptides. The devices of course may be coupled to regular light microscopes, monitors, data storing devices and the like. Said devices may be positioned according to the area to be monitored. Said area may e.g. be a single cell, a cell cluster in a certain area of a cell culture dish or a cell in a human or animal being, preferably a tissue comprised of several cells in a human or animal body being monitored by the method of the present invention. Any device capable of detecting fluorescent polypeptides known to the person skilled in the art may be used.

In step b) of the method of the present invention, the level of a fluorescent reporter polypeptide is detected before a cell is contacted with a compound influencing the expression of a gene of interest. Then, in a subsequent step, the reporter polypeptide is again detected after said compound influencing the expression of a gene of interest has been contacted with said cell. Thus, two different levels of reporter polypeptides may be detected. It is then possible to "compare" these two levels as outlined in step e). However, the present invention is not meant to be exclusively dependent on two detection steps. In further preferred embodiment of the present invention, it is possible to repeat the second detection step at least 2, 3, 4, 5, 6, 10 or 100 times in order to gain data over time. Thus, in one embodiment, the present invention is concerned with a method wherein the second detection step d) is carried out several times in order to determine a change in the expression of a gene of interest over time. Thus, in said embodiments, it is possible to analyse the levels of the reporter polypeptide over time.

It is in a further preferred embodiment also possible to record signals in real-time in order to obtain a movie of the readout, i.e. the detection of the fluorescent protein. This may be referred to as "live cell imaging" or "live tissue imaging".

Of course, the time points may be adjusted according to the compound influencing the expression of a gene of interest. For example, if a compound is known as acting slowly on the expression of a gene of interest, it might be helpful to detect the level of a fluorescent reporter polypeptide after an additional time of e.g. of 5, 10, 20, or 60 minutes upon introduction of said compound. In case a fast acting compound is used, the second detection step may be executed within seconds upon compound-introduction.

Furthermore, the term "comparing" should be understood as comparing the relative amounts of the reporter polypeptides in the at least two detection steps. In one preferred embodiment, the invention describes a method as outlined above wherein the comparison step e) is done by analyzing the relative amounts of the reporter peptides detected in steps b) and d). Thus, it is not necessary to quantify the absolute amounts of said polypeptides. However, when using such relative amounts, it needs to be ensured that the amounts are normalised against a control or a value which is identical in the at least two detection steps in order to obtain normalized relative amounts.

The term "assigning the change" in the context of the present invention means that after said comparison, the difference and differences, respectively, in the at least two detection steps are expressed e.g. as percentages. This may include a decrease in percentages or an increase in percentages of reporter polypeptide over a certain detection time. It may also lead to the conclusion that the level of reporter polypeptide has not changed over time or between two time points when detecting the at least two reporter polypeptides.

The method of the present invention may be used either in vivo or in vitro.

In the "in vivo situation", the cell mentioned in the method of the present invention may be part of a tissue of a human or animal being or may be a cell circulating in the body of a human or animal being. In this context, not only a single cell, but preferably cells of a certain tissue or cells suspicious of or known to be causative for a certain disease may be the targets of the present invention. As outlined above, misregulation of certain important cellular regulators (e.g. cell cycle regulators such as pRB, cyclins, CdKs, and so on) may lead to diseases such as e.g. cancer. In the in vivo-setup, the method according to the present invention may be used to monitor the expression of a gene of interest in e.g. cancerous tissue or a tumour when a compound influencing said expression is administered. Preferred embodiments of this in vivo situation according to the present invention will be described in detail below.

Thus, in a preferred embodiment, the present invention describes a method of non-invasively monitoring in vivo the expression of a gene of interest in a cell comprising at least the steps of:
  a) Introducing a nucleic acid molecule comprising:
    aa) a promoter sequence;
    bb) operatively linked thereto a sequence encoding said gene of interest polypeptide;
    cc) operatively fused thereto a sequence encoding a fluorescent reporter polypeptide;
  into said cell;
  b) Detecting the fluorescent reporter polypeptide in said cell by a non-invasive optical imaging method;
  c) Contacting said cell with a compound influencing the expression of said gene of interest;
  d) Detecting the fluorescent reporter polypeptide in said cell by a non-invasive optical imaging method upon step c);
  e) Comparing the level of fluorescent reporter polypeptide detected in step b) to the level of fluorescent reporter polypeptide detected in step d);
  f) Assigning the change in the expression of said gene of interest induced by said compound based on the comparison in step e).

The present invention describes in a preferred embodiment of this in vivo-setup a method as outlined above wherein said nucleic acid molecule and/or said compound influencing the expression of a gene of interest (e.g. an RNAi) may be introduced into said cell by transfection with the help of sonoporation, local injection or liposomal bags carrying antibodies to the host cell antigens for correct targeting, identification and localization, or mixtures thereof. Such techniques are known to the person skilled in the art.

Furthermore, the present invention refers in a preferred in vivo-embodiment to a method wherein the fluorescent reporter polypeptide encoded by the reporter sequence is chosen depending on the depth of the tissue to be monitored, i.e. for superficial tissue the fluorescent protein is chosen from blue, green or cyan fluorescent proteins and for deep tissue from red or infrared fluorescent proteins.

The method of the present invention may also be used in vitro. Such an in vitro-setup refers preferably to systems using mammalian cells cultured in cell/tissue culture systems or cells extracted from the human or animal body and used and/or treated outside the human or animal body.

"Mammalian cell culture systems" according to the present invention encompass all cell lines known and used by the person skilled in the art. These cell lines may be human, murine, rat, hamster or chicken cell lines and may be cultured according to standard techniques. Of course, different human cell lines may be used, as e.g. HeLa cells, 293 cells, WI-38 cells, U2OS cells and so on.

Thus, one embodiment of the present invention comprises a method of non-invasively monitoring the expression of a gene of interest in a cell comprising at least the steps of:
a) Introducing a nucleic acid molecule comprising:
   aa) a promoter sequence;
   bb) operatively linked thereto a sequence encoding said gene of interest polypeptide;
   cc) operatively fused thereto a sequence encoding a fluorescent reporter polypeptide;
   into a cell which is outside the human or animal body;
b) Detecting the fluorescent reporter polypeptide in said cell by a non-invasive optical imaging method;
c) Contacting said cell with a compound influencing the expression of said gene of interest;
d) Detecting the fluorescent reporter polypeptide in said cell by a non-invasive optical imaging method upon step c);
e) Comparing the level of fluorescent reporter polypeptide detected in step b) to the level of fluorescent reporter polypeptide detected in step d);
f) Assigning the change in the expression of said gene of interest induced by said compound based on the comparison in step e).

The present invention describes in a preferred embodiment of this in vitro-setup a method as outlined above wherein said nucleic acid molecule and/or said compound influencing the expression of a gene of interest (e.g. an RNAi) may be introduced into said cell by transfection with the help of sonoporation, liposomal bags, electroporation, or mixtures thereof. Such techniques are known to the person skilled in the art.

The change in the expression of a gene of interest monitored by a method according to the present invention may be an upregulation or a downregulation of said gene of interest. As set out above, this may be analysed either in vivo or in vitro. In a first situation or disease, a gene of interest may be downregulated and, thus, the goal may be the upregulation of said gene of interest and the monitoring of said upregulation. The second situation may be that a gene of interest is upregulated in a disease. In such a situation it may be the goal to downregulate the corresponding gene and monitor said downregulation by a method of the present invention. Preferred embodiments of the nucleic acid molecules as well as the methods according to the present invention for either situation are described in the following. These embodiments are meant to exemplify said situations. Thus, other compounds having the same overall effect of either downregulation or upregulation of the expression of a gene may be used.

In case a gene of interest is downregulated, the methods of the present invention may include in a preferred embodiment the use of a demethylating drug in order to upregulate such genes. In the converse situation, when downregulation of a gene of interest may be the goal, the methods of the present invention refer in preferred embodiments to the use of RNAi. These two groups of preferred embodiments will now be described in further detail.

In order to analyze whether a gene is downregulated/silenced due to DNA-methylation, differential methylation studies may be done prior to deciding on the therapy and prior to employing a method of monitoring of the invention. This may be done using fine needle aspiration cytology. DNA-samples may be obtained using this fine needle aspiration technique and analyzed for their methyl-groups. Such methods are known to the person skilled in the art.

In the following paragraphs, preferred embodiments of the present invention referring to nucleic acid molecules and methods monitoring the increase in the expression of a gene of interest are mentioned.

Thus, in one embodiment, the present invention refers to an isolated nucleic acid molecule comprising:
a) a methylated promoter sequence;
b) operatively linked thereto a sequence encoding a gene of interest polypeptide;
c) operatively fused thereto a sequence encoding a fluorescent reporter polypeptide.

The coding sequence comprised of sequences of b) and c) comprises a single start-codon at the 5'-end and a single stop-codon at the 3'-end. The term single start codon as used herein means that the sequence may comprise further internal ATG codons which, however, may not be used to iniate translation.

As already mentioned above, methylation of DNA, especially of promoters, is known to inhibit the expression of genes controlled by said promoters. Methylation of DNA is preferably understood as the methylation of bases, preferably of cytosines. A gene operatively coupled to a methylated promoter sequence may not be described and, thus, may not be active. For the above nucleic acid molecule, the corresponding coding sequence comprised of b) and c) will not be expressed if the promoter sequence is and remains methylated. However, if said region is no longer modified by methyl-groups, said sequence is a human promoter sequence identified by at least one human transcription factor inducing the expression of said coding region. Thus, a demethylation of said methylated promoted region will lead to an unmethylated region being capable of driving the expression of the gene which is operatively coupled to said region. The present invention comprises in one embodiment a nucleic acid molecule as just described wherein upon the action of a demethylating drug the unmethylated promoter sequence is a human promoter identified by at least one human transcription factor inducing the expression of the coding sequence. In a preferred embodiment, said methylated promoter of the nucleic acid molecule is identical to the endogenous methylated promoter of the gene of interest.

In a preferred embodiments of the present invention, the claimed nucleic acid molecule as described in the paragraphs above comprises a gene of interest sequence wherein the gene of interest is a tumour-suppressor gene or a gene suspicious of being causative for a disease due to its silencing. In one example of such an embodiment, the gene of interest may be RB. In other cases, the gene of interest may be CADM1, ZMYND10, RASSF5, PTEN, SERPINB5, EPB41L3, DAPK1 and the like.

Said construct/nucleic acid molecule may in further embodiments be used either in an in vivo method or in in vitro method according to the invention.

The term "demethylating drug" or "demethylating compound" as used herein is meant to encompass any drug capable of DNA-demethylation, i.e. the removal of methyl-groups from DNA and preferably from cytosines, in a cell. Said compound may be selected from the group of compounds comprising 5-azacytidine and the like. The systematic IUPAC name of 5-azacytidine is 4-amino-1-[3,4-dihydroxy-5-(hydroxymethyl) oxolan-2-yl]-1,3,5-triazin-2-one). Said chemical analogue of cytidine is incorporated into DNA and RNA during DNA replication and DNA transcription, respectively. This incorporation inhibits the activity of methyltransferase enzymes such as e.g. DNMT1. Thus, the incorporation results in demethylation. Of course, the person skilled in the are is aware of other cytidine-analogs and/or compounds acting similar to 5-azacytidine such as 5-aza-2'deoxycytidine, 1-(beta-D-ribofuranosyl), dehydro-5-azacytidine, [1-(beta-D-ribofuranosyl)-1,2-dihydropyrimidin-2-one], which is also known as Zebularine, and the like. Their mechanisms of action may also be based on inhibiting methyltransferases by forming complexes and/or the depletion of methyltransferases and so on. As already stated above, the effect of such drugs on methylated promoter regions is the activation of the controlled gene.

In a preferred embodiment, the present invention thus relates to a method of non-invasively monitoring in vivo the expression of a gene of interest in a cell comprising at least:
a) Introducing a nucleic acid molecule comprising:
  aa) a methylated promoter sequence;
  bb) operatively linked thereto a sequence encoding said gene of interest polypeptide;
  cc) operatively fused thereto a sequence encoding a fluorescent reporter polypeptide;
  into said cell;
b) Detecting the fluorescent reporter polypeptide in said cell by a non-invasive optical imaging method;
c) Contacting said cell with a demethylating drug;
d) Detecting the fluorescent reporter polypeptide in said cell by a non-invasive optical imaging method upon step c);
e) Comparing the level of fluorescent reporter polypeptide detected in step b) to the level of fluorescent reporter polypeptide detected in step d);
f) Assigning the increase in the expression of said gene of interest induced by the demethylating drug based on the comparison in step e).

In another preferred embodiment, the present invention relates to a method comprising at least the steps of:
a) Introducing a nucleic acid molecule comprising:
  aa) a methylated promoter sequence;
  bb) operatively linked thereto a sequence encoding said gene of interest polypeptide;
  cc) operatively fused thereto a sequence encoding a fluorescent reporter polypeptide;
  into a cell which is outside the human or animal body;
b) Detecting the fluorescent reporter polypeptide in said cell by a non-invasive optical imaging method;
c) Contacting said cell with a demethylating drug;
d) Detecting the fluorescent reporter polypeptide in said cell by a non-invasive optical imaging method upon step c);
e) Comparing the level of fluorescent reporter polypeptide detected in step b) to the level of fluorescent reporter polypeptide detected in step d);
f) Assigning the increase in the expression of said gene of interest induced by the demethylating drug based on the comparison in step e).

In both the in vivo and in vitro context, the present invention describes in a preferred embodiment a method wherein the dosage of the demethylating drug may be increased or decreased according to the assignment in step f) as listed above. Furthermore, the present invention also describes in a preferred embodiment a method wherein different demethylating drugs may be tested separately or in combination in order to obtain the most potent increase in the expression of said gene of interest according to the assignment in step f) as listed above.

The downregulation of a gene of interest may also be due to conformational restrictions of the corresponding DNA sequence. It is known that a closed conformation particularly in promoter regions may negatively influence gene expression. Said closed or "packed" conformation of the DNA seems to correlate with the acetylation state of the DNA. Thus, acetyl-groups on DNA seem to result in a more open DNA conformation and thus positively influence gene expression. Such acetyl-groups are transferred to the DNA via histone-acetyl-transferases (HATs) and are removed from the DNA by histone-deacetylases (HDACs). By inhibiting HDACs, the acetylation state of the DNA may increase and thus gene expression may be upregulated. Typical HDAC-inhibitors used in a method of the present invention may be 3-(1-Methyl-4-phenylacetyl-1H-2-pyrrolyl)-N-hydroxy-2-propenamide, Cyclo[(2S)-2-amino-8-oxodecanoyl-1-methoxy-L-tryptophyl-L-isoleucyl-(2R)-2-piperidinexcarbonyl], Sodium Butyrate, 4,5:8,9-Dianhydro-1,2,6,7,11-pentadeoxy-D-threo-D-ido-undeca-1,6-dienitol, 6-(1,3-Dioxo-1H,3H-benzo[de]isoquinolin-2-yl)-hexanoic acid hydroxyamide, 2-[(2-Hydroxynaphthalen-1-ylmethylene) amino]-N-(1-phenethyl)benzamide, [R-(E,E)]-7-[4-(Dimethylamino)phenyl]-N-hydroxy-4,6-dimethyl-7-oxo-2,4-heptadienamide and the like. These inhibitors are provided by e.g. SigmaAldrich (see http://www.sigmaaldrich.com/Area_of_Interest/Life_Science/Cell_Signaling/Product_Highlights/Histone_Deacetylase_Inhibitors.html).

Other examples of HDAC-inhibitors are PXD101 (also referred to as Belinostat) and SAHA. Particularly in this embodiment of the invention, the promoter region of the nucleic acid molecule used in a method of the present invention corresponds to the endogenous promoter of the gene of interest thus reflecting the DNA conformation of the endogenous promoter.

In a preferred embodiment, the present invention thus relates to a method of non-invasively monitoring in vivo the expression of a gene of interest in a cell comprising at least:
a) Introducing a nucleic acid molecule comprising:
  aa) the promoter sequence of said gene of interest;
  bb) operatively linked thereto a sequence encoding said gene of interest polypeptide;
  cc) operatively fused thereto a sequence encoding a fluorescent reporter polypeptide;
  into said cell;
b) Detecting the fluorescent reporter polypeptide in said cell by a non-invasive optical imaging method;
c) Contacting said cell with an HDAC-inhibitor;
d) Detecting the fluorescent reporter polypeptide in said cell by a non-invasive optical imaging method upon step c);
e) Comparing the level of fluorescent reporter polypeptide detected in step b) to the level of fluorescent reporter polypeptide detected in step d);
f) Assigning the increase in the expression of said gene of interest induced by the HDAC-inhibitor based on the comparison in step e).

In another preferred embodiment, the present invention relates to a method comprising at least the steps of:
a) Introducing a nucleic acid molecule comprising:
  aa) the promoter sequence of the gene of interest;
  bb) operatively linked thereto a sequence encoding said gene of interest polypeptide;
  cc) operatively fused thereto a sequence encoding a fluorescent reporter polypeptide;

into a cell which is outside the human or animal body;
b) Detecting the fluorescent reporter polypeptide in said cell by a non-invasive optical imaging method;
c) Contacting said cell with an HDAC-inhibitor;
d) Detecting the fluorescent reporter polypeptide in said cell by a non-invasive optical imaging method upon step c);
e) Comparing the level of fluorescent reporter polypeptide detected in step b) to the level of fluorescent reporter polypeptide detected in step d);
f) Assigning the increase in the expression of said gene of interest induced by the HDAC-inhibitor based on the comparison in step e).

In the following paragraphs, preferred embodiments of the present invention referring to nucleic acid molecules and methods for monitoring the decrease in the expression of a gene of interest will be mentioned.

Thus, in one embodiment, the present invention refers to a nucleic acid molecule of an in vivo method of the present invention comprising:
a) a promoter sequence;
b) operatively linked thereto a sequence encoding a non-functional polypeptide of a gene of interest;
c) operatively fused thereto a sequence encoding a fluorescent reporter polypeptide;
wherein the coding region comprised of b) and c) comprises at least one start-codon at the 5'-end and a single stop-codon at the 3'-end.

In a preferred embodiment of the present invention, the claimed nucleic acid molecule as described in the paragraphs above comprises a gene of interest sequence wherein the gene of interest is an oncogene or a proto-oncogene or a gene suspicious of being causative for a disease due to its overexpression. In one example of such an embodiment, the gene of interest may be Her-2neu. In further examples, the gene of interest may be VEGF, RAS, Wnt, MYC, ERK, TRK etc.

Referring to these preferred embodiments of the invention, it is obvious why the gene of interest-polypeptide may preferably be not functional in in vivo setups. In case it were functional, this would lead to an even increased overall expression of the gene (in most cases an oncogene) resulting from the overexpression of the endogenous gene and the exogenous gene of interest sequence. This may be harmful to the cells/tissue.

Thus, in a preferred embodiment relating to the nucleic acid molecule of the present invention and to the in vivo method, the gene of interest sequence encoding a non-functional polypeptide comprises either a part of the entire gene of interest sequence or the entire gene of interest sequence containing at least one insertion, at least one deletion, at least one nucleotide exchange, or mixtures thereof, in order to obtain a non-functional gene of interest polypeptide. However, it does not comprise stop-codons. Thus, a non-functional gene of interest-polypeptide may be obtained, e.g. by a frame-shift resulting from the at least one insertion or at least one deletion in the gene of interest sequence. It may also be obtained by a single nucleotide exchange resulting in a amino acid replacement in the corresponding polypeptide which leads to a disruption of the three-dimensional structure of the resulting protein. In case an oncogene is the gene of interest, one may delete sequences encoding functional parts of the resulting oncogene (such as a catalytic domain, a binding domain, a dimerization domain and so on) and use the remaining coding sequence as the gene of interest sequence in the nucleic acid molecule of the present invention. In doing so, the resulting polypeptide is not functional. The person skilled in the art is of course aware that multiple sequences may be removed and that the length of the removed sequence(s) may vary depending on the gene of interest.

In case the gene of interest encodes a transcription factor, the promoter sequence of the nucleic acid molecule as described in this aspect of the invention may in a further embodiment be a human promoter recognized solely by said human transcription factor encoded by the gene of interest. Thereby, in case a downregulation of said gene of interest is achieved, the expression of the coding sequence (and thus the fluorescent reporter polypeptide) will be also downregulated due to the decreased level of the gene of interest polypeptide being the corresponding transcription factor.

Said construct/nucleic acid molecule may in further embodiments be used either in an in vivo method or in an in vitro method according to the invention.

In this context, the present invention describes a method of monitoring the decrease of the expression of a gene of interest. Said decrease may be achieved by compounds/molecules comprising antisense RNA, shRNA, siRNA, miRNA or other nucleic acid molecules of comparable function which are in general referred to as "RNAi" or "RNA interference" or "inhibitor molecules". Said molecules may be additionally modified by e.g. nanoparticles.

Using such RNA interference strategies, it is crucial to use molecules that specifically interfere only with the expression of the gene of interest but not with the expression of another unrelated cellular factor. The selection, identification and production of such RNA-based inhibitors is well-known to the person skilled in the art.

Typically, one will identify sequences within the coding sequence of the gene of interest that may be accessible for an antisense strategy or an siRNA-based approach in view of the absence of e.g. secondary structural elements which would likely be prohibitive for in vivo interaction between the inhibitory RNA-based molecules and the respective mRNA. Such stretches of nucleic acids may be identified using computer programs such as SFOLD.

In a second step such sequences will then be compared with other sequences in order to determine whether they are unique for the respective gene of interest. This may be done be, e.g. performing BLAST searches at the National Center for Biotechnology Information (http://www.ncbi.nlm.nih.gov/).

Once one has identified unique sequences, antisense or siRNA inhibitors may be selected by using a complementary sequence that preferably exactly matches the identified sequences. Of course, lower degrees of complementarity may be used, provided that complementarity is not reduced to a level where unspecific interaction between antisense or siRNA-based inhibitors and messenger RNAs of other cellular factors are likely to occur.

Typically, complementarity grades between the inhibitory RNA-based molecules and the identified specific sequences will be at least 90%, at least 91%, at least 92%, at least 93%, at least 94%, at least 95%, at least 96%, at least 97%, at least 98% or at least 99%.

The term "complementarity" is of course well-known to the person skilled in the art as it relates to the basic properties of nucleic acid molecules hybridizing with each other in view of the ability of adenosine to pair with thymine and uracil and guanidine to pair with cytidine.

The person skilled in the art will, of course, understand that the nucleic acid sequence conferring complementarity with the complete coding sequence or parts thereof of the gene of interest must have a certain minimum length in order to ensure that the complementary sequence is indeed specific for the gene of interest.

Therefore, the nucleic acid sequence within the inhibitory molecule which confers complementarity to the gene of interest should be at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 50, at least 75, at least 100, at least 150, at least 200, at least 300 or at least 400 nucleotides in length and forming a contiguous stretch.

The person skilled in the art will of course also be aware that depending on the length of the nucleic acid sequence conferring complementarity to the coding sequences or parts thereof of the gene of interest, the minimum degree of complementarity which is necessary to ensure that the complementarity-conferring nucleic acid sequence indeed only specifically targets the gene of interest will vary. Thus, if a rather long nucleic acid molecule of 30, 50, 60, 75, 100 nucleotides is used, a lower degree of complementarity may be used and still ensure specificity between the inhibitory molecule and the coding sequence or parts thereof of the gene of interest, while of course a higher degree of complementarity will be necessary if the complementarity-conferring nucleic acid sequence within the inhibitory molecule comprises e.g. only a stretch of at least 14, 15, 16, 17, or 19 nucleotides.

As mentioned above, a decrease of the expression of a gene of interest may be achieved by "RNAi" or "RNA interference" or "inhibitor molecules" designed as generally outlined above.

One class of such inhibitor molecules may therefore be molecules comprising a recombinant nucleic acid molecule having a nucleic acid sequence which is complementary to the complete coding sequences or parts thereof of a gene of interest. The nucleic acid sequence molecules may be made of DNA, RNA or other nucleic acid based molecule, which, however, instead of nucleotides may comprise at least partially nucleotide analogues as long as the resulting molecule is capable of specifically hybridizing with the complete coding sequence or parts thereof of a gene of interest.

In a preferred embodiment, the above described inhibitory molecules preferably comprise antisense RNA, shRNA, siRNA, miRNA or other nucleic acid molecules of comparable function to the gene of interest.

These terms clearly indicate to the person skilled in the art how these molecules should be synthesized, what degree of complementarity should be considered, etc. It is to be understood that antisense RNAs as well shRNAs and siRNAs in accordance with the invention will fulfill the above mentioned criteria as to the length of these nucleic acid molecules, their degree of complementarity etc.

An antisense molecule will typically comprise a length of 10, 11, 12, 13, 14, 15, 16, 17, 18, 19, 20, 21, 22, 23, 24, 25, 26, 27, 28, 29, 30, 50, 70, 100, 150, 200, 300 or more nucleotides.

For the purposes of RNA interference so-called short hairpin RNA or synthetic double-stranded siRNA oligonucleotides may be used.

An siRNA molecule will typically comprise a length of 20, 21, 22, 23, 24 or 25 nucleotides.

Typically, as shRNA molecules are expressed, single-stranded RNA molecules that form an intramolecular hairpin structure. By intracellular processing through the enzyme Dicer, siRNA molecules are generated therefrom.

An intracellular transcription of shRNA molecules can be achieved if both strands of an shRNA duplex are expressed using an expression vector in the form of a single RNA molecule or DNA molecule. For this purpose, the transcribed RNA strand should ideally comprise 19 to 21 nucleotides of the sense shRNA sequence and ideally 19 to 21 nucleotides of the corresponding complementary sequence. Both sequences would ideally be separated e.g. by a six nucleotide long spacer.

It is well known that efficiency of siRNA mediated repression of cellular target transcripts is dependent on the choice of suitable siRNA sequences. Guidelines have been developed for the design of effective siRNA molecules. These guidelines have been typically derived for synthetic siRNA oligonucleotides, but should also apply for the processed form of shRNA molecules.

Other than shRNA molecules which are only obtained after expression and processing within the cells, synthetic siRNA oligonucleotides consist of double-stranded RNA molecules which are typically between 19 to 21 nucleotides long. These siRNA molecules may e.g. be transfected into cellular systems as mentioned above and will thus initiate an RNAi process.

Determination of the targeted sequence and siRNA sequence motif may e.g. be determined according to well known publications such as those by Tuschl et al. Thus, one may use the coding region of a target mRNA for identification of suitable siRNA target sequences only. While it is preferred that the selected siRNA sequence motif is directed to the coding region of the target mRNA, it may also be designed against the regulatory regions of a gene of interest such as the 5' and 3' untranslated regions.

If coding sequences of a messenger RNA are used as target sequences, one may typically use sequences starting 70 nucleotides downstream of the start codon and ending 50 nucleotides upstream of the stop codon.

This sequence area may then be searched for the sequence motive AA (N19) in which N designates any nucleotide. The resulting siRNA sequence will then comprise 19 nucleotides following the motive AA and preferably two additionally added uridine or thymidine residues. In the case of synthetic siRNA oligonucleotides, the uridine residues may preferably be replaced by thymidine.

In another approach, guidelines may be used according to Reynolds et al.

Reynolds et al. have suggested the following criteria for selecting potential shRNA or synthetic siRNA target sequences:

1. the 30-50% guanine-cytosine content
2. at least three adenines or uracils at positions 15 to 19 of the sense strand
3. absence of intermolecular hairpin structures
4. adenine at position 19 of the sense strand
5. adenine at position 3 of the sense strand
6. uracil at position 10 of the sense strand
7. no guanine or cytosine at position 19 of the sense strand
8. no guanine at position 13 of the sense strand.

These eight criteria may be weighed according to the following scheme:
  (i) 1 point for criteria 1, 3, 4, 5 and 6
  (ii) 1 point for each adenine or uridine at position 15 to 19, at least 3 corresponding bases (criterion 2)
  (iii) non-fulfilment of criteria 7-8 result in −1 point each.

According to Reynolds, only siRNA or shRNA sequences should be considered which according to this scheme have a point value of at least 6. Such siRNA sequences may then be used for a homology search using the BLAST program.

Following this approach, siRNAs may be excluded that as a matter of their homology with other coding mRNA sequences would lead to non-specific repression of target structures.

If siRNA or shRNA sequences have been identified this way, they may be cloned into an expression plasmid. Thus, the RNA sequences may be cloned into the plasmid pSuppressor (pSHH, Imgenex, San Diego, Calif., USA). For cloning the siRNA sequences into the pSHH constructs, hybridised DNA oligonucleotides can be used that comprise the siRNA sense sequence, a spacer, the corresponding antisense sequence and the termination sequence.

In a preferred embodiment, the present invention thus relates to a method of non-invasively monitoring in vivo the expression of a gene of interest in a cell comprising at least the steps of:
  a) Introducing a nucleic acid molecule comprising:
    aa) a promoter sequence;
    bb) operatively linked thereto a sequence encoding a non-functional polypeptide of said gene of interest;
    cc) operatively fused thereto a sequence encoding a fluorescent reporter polypeptide;
  into said cell;
  b) Detecting the fluorescent reporter polypeptide in said cell by a non-invasive optical imaging method;
  c) Contacting said cell with RNAi tailored against said gene of interest;
  d) Detecting the fluorescent reporter polypeptide in said cell by a non-invasive optical imaging method upon step c);
  e) Comparing the level of fluorescent reporter polypeptide detected in step b) to the level of fluorescent reporter polypeptide detected in step d);
  f) Assigning the decrease in the expression of said gene of interest induced by the RNAi based on the comparison in step e).

In another preferred embodiment, the present invention relates to a method comprising at least the steps of:
  a) Introducing a nucleic acid molecule comprising:
    aa) a promoter sequence;
    bb) operatively linked thereto a sequence encoding said gene of interest polypeptide;
    cc) operatively fused thereto a sequence encoding a fluorescent reporter polypeptide;
  into a cell which is outside the human or animal body;
  b) Detecting the fluorescent reporter polypeptide in said cell by a non-invasive optical imaging method;
  c) Contacting said cell with RNAi tailored against said gene of interest;
  d) Detecting the fluorescent reporter polypeptide in said cell by a non-invasive optical imaging method upon step c);
  e) Comparing the level of fluorescent reporter polypeptide detected in step b) to the level of fluorescent reporter polypeptide detected in step d);
  f) Assigning the decrease in the expression of said gene of interest induced by the RNAi based on the comparison in step e).

In the context of monitoring the effect of RNAi in a cell outside the human or animal body, one embodiment of the present invention relates to a method of targeting the RNAi in step c) to a cell which already expresses the reporter polypeptide; into said cell, the nucleic acid molecule has thus already been introduced. Said embodiment comprises either a second nucleic acid molecule comprising a second coding sequence or a second coding sequence on the first nucleic acid molecule wherein said second coding sequence is operatively coupled to a strong, constitutive promoter. In case it is a second molecule, it is introduced into the cell along with the first nucleic acid molecule. Said second coding region encodes a transmembrane protein which is also expressed upon introduction. Thus, a cell expressing the gene of interest polypeptide and the reporter polypeptide is also expressing the transmembrane protein. The protein is targeted to the membrane by cellular localizing and processing signals. The extracellular part of said transmembrane protein, however, is artificial and thus usually not present on the outside of a cell. Thus, this extracellular part "marks" the cell as having already internalized and expressed the nucleic acid molecule of step a). It may also serve as docking site for any antibodies targeted specifically to this extracellular part of the transmembrane protein. Such antibodies may easily be obtained by standard procedures known to the skilled person. In order to now specifically target the RNAi in step c) to and into a cell already expressing the coding sequence of the nucleic acid molecule, the artificial part of the transmembrane protein may be used as anchoring region. As mentioned above, the RNAi may be introduced by transfection techniques, inter alia by methods using liposomal bags carrying antibodies to the outside antigens of a cell. These antibodies may be directed against the extracellular part of the transmembrane protein and thus the RNAi is specifically targeted to their target cells.

It needs to be understood that in any method according to the present invention referring to RNAi, the gene of interest sequence of the nucleic acid molecule used in said method comprises at least the region of the gene of interest the RNAi is tailored against.

In both the in vivo and in vitro context, the present invention describes in a preferred embodiment a method wherein the dosage of the RNAi may be increased or decreased according to the assignment in step f) as listed above. Furthermore, the present invention also describes in a preferred embodiment a method wherein different RNAi's tailored against one gene of interest may be tested separately or in combination in order to obtain the most potent increase in the expression of said gene of interest according to the assignment in step f) as listed above.

In a further aspect, the invention relates to the use of a method and/or a nucleic acid as described above.

In one embodiment concerning the in vivo setup, the invention thus relates to the use of a method for monitoring the increase in the expression of a gene of interest induced by e.g. a demethylating drug over time in vivo when treating a disease with e.g. a demethylating drug. Thus, the method may be used for monitoring the therapeutic effect of the demethylating drug. Correspondingly, the invention relates in a further embodiment to the use of a method for monitoring the decrease in the expression of a gene of interest induced by RNAi over time in vivo when treating a disease by RNAi. Here, the method may be used for monitoring the therapeutic effect of the RNAi. Obviously, in the case of RNAi, the first detection step should give rise to a signal in the optical imaging method as otherwise a decrease could not be detected. Thus, in case there is no reporter polypeptide detected in the first detection step, the conditions of the preceding steps may be optimized in order to find suitable conditions wherein detection is possible. Only then the therapeutic compound may be administered.

In case a functional gene of interest polypeptide is expressed by the nucleic acid molecule of the invention, said functional gene of interest polypeptide may also be used as therapeutic. As outlined above, in case of silencing of genes in e.g. cancer, tumour-suppressor genes are often found to be silenced. This may be treated by a demethylating drug or an HDAC-inhibitor and monitored by a method of the present invention. When using said method, a functional tumour-suppressor polypeptide may be introduced encoded by the gene of interest sequence and exert additional positive therapeutic effects.

Also, in one embodiment, the method according to the invention may be used for adjusting the dosage of a demethylating drug or an RNAi in order to obtain a decrease or increase in the expression of a gene of interest. Furthermore, the method may be used for testing different methylating agents or RNAi's in order to identify the most potent demethylating drug/RNAi separately or in combination with other demethylating drugs and RNAi's, respectively. This applies to both the in vivo and the in vitro situation. In in vitro setups like cell culture systems as mentioned above, the method of the invention may preferably be used in order to screen for compounds having an impact on the change of the expression of a gene of interest. Thus, it may be used as rapid screening system for testing drugs possibly acting on gene expression.

A method or a nucleic acid molecule according to the invention may in one embodiment be used for the delivery of a demethylating drug as well as monitoring the delivery of said drug and monitoring the increase in the expression of a gene of interest induced by said drug at the same time. Correspondingly, a method or a nucleic acid molecule according to the invention may in another embodiment be used for delivering an RNAi, monitoring the delivery of said RNAi as well as monitoring the decrease in the expression of a gene of interest induced by said RNAi at the same time. This again applies to both the in vivo and the in vitro situation.

Further preferred embodiments of the invention relate to:

1. A method of non-invasively monitoring the expression of a gene of interest in a cell comprising at least the steps of:
   a) Introducing a nucleic acid molecule comprising:
      aa) a promoter sequence;
      bb) operatively linked thereto a sequence encoding said gene of interest polypeptide;
      cc) operatively fused thereto a sequence encoding a fluorescent reporter polypeptide;
   into said cell;
   b) Detecting the fluorescent reporter polypeptide in said cell by a non-invasive optical imaging method;
   c) Contacting said cell with a compound influencing the expression of said gene of interest;
   d) Detecting the fluorescent reporter polypeptide in said cell by a non-invasive optical imaging method upon step c);
   e) Comparing the level of fluorescent reporter polypeptide detected in step b) to the level of fluorescent reporter polypeptide detected in step d);
   f) Assigning the change in the expression of said gene of interest induced by said compound based on the comparison in step e).

2. A method according to 1 of non-invasively monitoring in vivo the expression of a gene of interest in a cell comprising at least the steps of:
   a) Introducing a nucleic acid molecule comprising:
      a. a methylated promoter sequence;
      b. operatively linked thereto a sequence encoding said gene of interest polypeptide;
      c. operatively fused thereto a sequence encoding a fluorescent reporter polypeptide;
   into said cell;
   b) Detecting the fluorescent reporter polypeptide in said cell by a non-invasive optical imaging method;
   c) Contacting said cell with a demethylating drug;
   d) Detecting the fluorescent reporter polypeptide in said cell by a non-invasive optical imaging method upon step c);
   e) Comparing the level of fluorescent reporter polypeptide detected in step b) to the level of fluorescent reporter polypeptide detected in step d);
   f) Assigning the increase in the expression of said gene of interest induced by the demethylating drug based on the comparison in step e).

3. A method according to 1 comprising at least the steps of:
   a) Introducing a nucleic acid molecule comprising:
      aa) a methylated promoter sequence;
      bb) operatively linked thereto a sequence encoding said gene of interest polypeptide;
      cc) operatively fused thereto a sequence encoding a fluorescent reporter polypeptide;
   into a cell which is outside the human or animal body;
   b) Detecting the fluorescent reporter polypeptide in said cell by a non-invasive optical imaging method;
   c) Contacting said cell with a demethylating drug;
   d) Detecting the fluorescent reporter polypeptide in said cell by a non-invasive optical imaging method upon step c);
   e) Comparing the level of fluorescent reporter polypeptide detected in step b) to the level of fluorescent reporter polypeptide detected in step d);
   f) Assigning the increase in the expression of said gene of interest induced by the demethylating drug based on the comparison in step e).

4. A method according to 1 of non-invasively monitoring in vivo the expression of a gene of interest in a cell comprising at least the steps of:
   a) Introducing a nucleic acid molecule comprising:
      aa) a promoter sequence;
      dd) operatively linked thereto a sequence encoding a non-functional polypeptide of said gene of interest;
      ee) operatively fused thereto a sequence encoding a fluorescent reporter polypeptide;
   into said cell;
   b) Detecting the fluorescent reporter polypeptide in said cell by a non-invasive optical imaging method;
   c) Contacting said cell with RNAi tailored against said gene of interest;
   d) Detecting the fluorescent reporter polypeptide in said cell by a non-invasive optical imaging method upon step c);
   e) Comparing the level of fluorescent reporter polypeptide detected in step b) to the level of fluorescent reporter polypeptide detected in step d);
   f) Assigning the decrease in the expression of said gene of interest induced by the RNAi based on the comparison in step e).

5. A method according to 1 comprising at least the steps of:
   a) Introducing a nucleic acid molecule comprising:
      a. a promoter sequence;
      b. operatively linked thereto a sequence encoding said gene of interest polypeptide;

c. operatively fused thereto a sequence encoding a fluorescent reporter polypeptide;
   into a cell which is outside the human or animal body;
b) Detecting the fluorescent reporter polypeptide in said cell by a non-invasive optical imaging method;
c) Contacting said cell with RNAi tailored against said gene of interest;
d) Detecting the fluorescent reporter polypeptide in said cell by a non-invasive optical imaging method upon step c);
e) Comparing the level of fluorescent reporter polypeptide detected in step b) to the level of fluorescent reporter polypeptide detected in step d);
f) Assigning the decrease in the expression of said gene of interest induced by the RNAi based on the comparison in step e).

6. A method according to any of 1 to 5 wherein said nucleic acid molecule and/or said RNAi is introduced into said cell by transfection with the help of sonoporation, local injection or liposomal bags carrying antibodies to the host cell antigens for correct targeting, identification and localization, or mixtures thereof.

7. An isolated nucleic acid molecule comprising:
a) a methylated promoter sequence;
b) operatively linked thereto a sequence encoding a gene of interest polypeptide;
c) operatively fused thereto a sequence encoding a fluorescent reporter polypeptide;
   wherein the coding sequence comprised of b) and c) comprises a single start-codon at the 5'-end and a single stop-codon at the 3'-end.

8. A nucleic acid molecule according to 7 wherein the gene of interest is a tumour suppressor-gene or a gene suspicious of being causative for a disease due to its silencing.

9. An isolated nucleic acid molecule comprising:
a) a promoter sequence;
b) operatively linked thereto a sequence encoding a non-functional polypeptide of a gene of interest;
c) operatively fused thereto a sequence encoding a fluorescent reporter polypeptide;
   wherein the coding sequence comprised of b) and c) comprises a single start-codon at the 5'-end and a single stop-codon at the 3'-end.

10. A nucleic acid molecule according to 9 wherein the gene of interest sequence encoding a non-functional polypeptide comprises either a part of the entire gene of interest sequence or the entire gene of interest sequence containing at least one insertion, at least one deletion, at least one nucleotide exchange, or mixtures thereof, in order to obtain a non-functional gene of interest polypeptide, but wherein the gene of interest sequence does not comprise stop-codons.

11. A nucleic acid molecule according to 9 and 10 wherein the gene of interest is an oncogene, a proto-oncogene or a gene suspicious of being causative for a disease due to its overexpression.

12. Use of a method according to any of 1 to 6 for monitoring the expression of a gene of interest in a cell over time when contacting said cell with a compound influencing the expression of said gene of interest and thus for monitoring the effect of said compound.

13. Use of a method according to any of 1 to 6 for delivering a compound influencing the expression of a gene of interest in a cell, monitoring the delivery of said compound as well as monitoring the influence on the expression of said gene of interest induced by said compound at the same time.

14. Use of a method according to any of 1 to 6 for adjusting the dosage of a compound influencing the expression of a gene of interest in order to obtain a further change in the expression of said gene of interest.

15. Use of a method according to 2 and 3 for testing different demethylating drugs in order to identify the most potent demethylating drug separately or in combination.

16. Use of a method according to 4 and 5 for testing different RNAi's tailored against one gene of interest in order to identify the most potent RNAi separately or in combination.

17. Use of a nucleic acid molecule according to 7 to 11 for monitoring the expression of a gene of interest in a cell over time when contacting said cell with a compound influencing the expression of said gene of interest and thus for monitoring the effect of said compound.

13. Use of a nucleic acid molecule according to 7 to 11 for delivering a compound influencing the expression of a gene of interest in a cell, monitoring the delivery of said compound as well as monitoring the influence on the expression of said gene of interest induced by said compound at the same time.

14. Use of a nucleic acid molecule according to 7 to 11 for adjusting the dosage of a compound influencing the expression of a gene of interest in order to obtain a further change in the expression of said gene of interest.

15. Use of a nucleic acid molecule according to 7 to 11 for testing different demethylating drugs in order to identify the most potent demethylating drug separately or in combination.

16. Use of a nucleic acid molecule according to 7 to 11 for testing different RNAi's tailored against one gene of interest in order to identify the most potent RNAi separately or in combination.

It is understood that the example and figures are not to be construed as limiting. The skilled person in the art will clearly be able to envisage further modifications of the principles laid out herein.

Example

Protocol for a Method of Non-Invasively Monitoring the Expression of Her-2neu (a Gene Known to be Overexpressed in Breast Cancer) in Breast Cancer Tissue when Transfecting RNAi Tailored Against Her-2neu into Said Tissue A schematic drawing of the steps is depicted in FIG. 1.

Step 1: A DNA-construct as is prepared. Said construct comprises a human promoter which is known to be active in breast cancer tissue. Operatively linked to said promoter is a coding region. This coding region is comprised of the Her-2neu-gene fused to the gene of a fluorescent protein (e.g. GFP). The Her-2neu sequence is modified such that a non-functional polypeptide of Her-2neu is expressed, e.g. by a frame-shift mutation. At the 3'-end, the sequence of the fluorescent protein gene is fused to the Her-2neu sequence such that the resulting protein is transcribed as one fusion protein and that the resulting fluorescent polypeptide is functional. This means that in the present example the frame-shift mutation introduced in the Her-2neu sequence is compensated by a further frame-shift mutation introduced at the beginning of the sequence coding for the fluorescent protein in order to encode a functional fluorescent protein, e.g. GFP.

Step 2: The construct as described above is then transfected into the breast cancer tissue, e.g. by means of injecting a liposomal bag carrying the construct and preferably antibodies directed to antigens of breast cancer cells for means of targeting. It should be noted that this targeting step may be beneficial for the following visualization step as only cancerous tissue is detected. However, this may also be achieved in case the promoter as described above is only functional in breast cancer cells and thus the coding region (and, therefore, the fluorescent protein) is expressed only in these cells. In either case, the fusion gene is expressed in the cancerous cells comprising a non-functional domain of Her-2neu as well as a functional fluorescent protein domain, e.g. GFP.

Step 3: The fluorescent protein domain is visualized and thus the breast cancer tissue lightens up. This may be done by using optical imaging devices exciting the fluorescent protein at a certain wavelength followed by detection of the emitted light at the corresponding wavelength. UV-light may be used to excite GFP followed by detection of the emitted light as green colour. Preferably, one may use compounds that are excited by infra red light and/or compounds such as bright far-red fluorescent protein [disclosed e.g. in Shcherbo D. et al., Nature Methods 4, 741-746 (2007)]

Step 4: Double stranded RNAi tailored against Her-2neu is then transfected into the breast cancer tissue. This may again be done by means of injecting a liposomal bag carrying the RNAi-construct and preferably antibodies directed to antigens of breast cancer cells for means of targeting.

Step 5: The expression of the fusion gene introduced in step 2 is now blocked as well as the expression of the endogenous Her-2neu-gene. This is achieved by the RNAi selectively blocking translation from the corresponding mRNA. Due to the fusion of the Her-2neu gene to the sequence coding for the fluorescent protein, the expression of the fluorescent protein is also blocked. Thus, no fluorescent protein at all or only a minor amount of the fluorescent protein is present in the breast cancer tissue upon transfection of the RNAi.

Step 6: Again, the fluorescent protein domain is visualized in the corresponding tissue. As set out above, UV-light may be used to excite GFP followed by detection of the emitted light as green colour. Preferably, one may also use compound that are excitated by infra red light. In case of a total translational block of the mRNA transcribed from the fusion gene by the introduced RNAi, no fluorescent protein is detectable. Thus, the breast cancer tissue can not be visualized any more. In case of a decrease, the signal is weaker compared to the signal detected in step 3. Overall, this strongly suggests that the endogenous Her-2neu expression is also blocked and, thus, that a regression of the tumour has been achieved.

In summary, the therapeutic effect of the RNAi is monitored in vivo in breast cancer tissue in a non-invasive manner.

The invention claimed is:

1. A method of non-invasively monitoring in vivo the expression of a gene of interest in a cell, comprising:
    a) introducing a nucleic acid molecule comprising:
        a methylated promoter sequence;
        operatively linked thereto a sequence encoding a gene of interest polypeptide selected from the group of polypeptides comprising CADM1, Rb, ZMYND10, RASSF5, PTEN, SERPINB5, EPB41L3, and DAPK1;
        operatively fused thereto a sequence encoding a fluorescent reporter polypeptide; into said cell;
    b) detecting the fluorescent reporter polypeptide in said cell by a non-invasive optical imaging method;
    c) contacting said cell with a demethylating drug;
    d) detecting the fluorescent reporter polypeptide in said cell by a non-invasive optical imaging method upon step c);
    e) comparing the level of fluorescent reporter polypeptide detected in step b) to the level of fluorescent reporter polypeptide detected in step d);
    f) assigning the change in the expression of said gene of interest induced by said demethylating drug based on the comparison in step e).

2. The method according to claim 1, further including: monitoring the expression of said gene of interest in said cell over time.

3. The method according to claim 1, further including: monitoring the contact of said demethylating drug as well as monitoring the influence on the expression of said gene of interest induced by said demethylating drug at the same time.

4. The method according to claim 1, further including: adjusting the dosage of said demethylating drug in order to obtain a further change in the expression of said gene of interest.

5. The method according to claim 1, further including: testing different demethylating drugs in order to identify the most potent demethylating drug separately or in combination.

6. The method according to claim 1, further including: modifying the sequence encoding the gene of interest polypeptide to encode a non-functional polypeptide.

7. The method according to claim 6, wherein modifying the sequence encoding the gene of interest polypeptide is performed by introducing a frame shift mutation.

8. The method according to claim 1, further including modifying the sequence encoding the gene of interest polypeptide and the sequence encoding the fluorescent reporter polypeptide to encode for a non-functional gene of interest polypeptide and a functional fluorescent reporter polypeptide.

9. The method according to claim 1, wherein the sequence encoding a fluorescent reporter polypeptide is chosen depending on the depth of the tissue to be monitored.

10. The method according to claim 9, further including using at least one of blue, green, or cyan fluorescent proteins for superficial tissue and at least one of red or infrared fluorescent proteins for deep tissue.

11. The method according to claim 6, wherein the non-functional polypeptide is at least one of CADM1 and Rb.

* * * * *